US008697351B2

(12) United States Patent
Yabusaki (10) Patent No.: US 8,697,351 B2
(45) Date of Patent: Apr. 15, 2014

(54) METHOD FOR MEASUREMENT OF PHYSIOLOGICALLY ACTIVE SUBSTANCE DERIVED FROM ORGANISM AND MEASUREMENT APPARATUS

(75) Inventor: Katsumi Yabusaki, Hamamatsu (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 425 days.

(21) Appl. No.: 13/056,100

(22) PCT Filed: Jul. 28, 2009

(86) PCT No.: PCT/JP2009/063405
§ 371 (c)(1),
(2), (4) Date: Jan. 26, 2011

(87) PCT Pub. No.: WO2010/013702
PCT Pub. Date: Feb. 4, 2010

(65) Prior Publication Data
US 2011/0124036 A1 May 26, 2011

(30) Foreign Application Priority Data

Jul. 30, 2008 (JP) ................................. 2008-196809

(51) Int. Cl.
*C12Q 1/00* (2006.01)
(52) U.S. Cl.
USPC .......................................................... 435/4
(58) Field of Classification Search
USPC .......................................................... 435/4
See application file for complete search history.

(56) References Cited

U.S. PATENT DOCUMENTS 3,915,805 A 10/1975 Levin

FOREIGN PATENT DOCUMENTS

| EP | 0 347 951 | 12/1989 |
| EP | 0 957 366 | 11/1999 |
| EP | 1 312 613 | 5/2003 |
| EP | 1 450 160 | 8/2004 |
| EP | 2 081 024 | 7/2009 |
| JP | 61-93958 | 5/1986 |
| JP | 09-159671 | 6/1997 |
| JP | 10-293129 | 11/1998 |
| JP | 11-290095 | 10/1999 |
| JP | 2003-155298 | 6/2003 |
| JP | 2004-061314 | 2/2004 |
| JP | 2004-117127 | 4/2004 |
| JP | 2004-251807 | 9/2004 |
| WO | WO 2008/038329 | 4/2008 |

OTHER PUBLICATIONS

Lee et al. "In vitro bioassay of endotoxin using fluorescein as a pH indicator in a macrophage cell culture system", Yonsei Medical Journal, 2005, 46(2):268-274.*
Mitsumoto et al. "Novel endotoxin assay by laser light-scattering particle-counting method", J of Clinical Laboratory Analysis, 2009, 23:117-124. Published onlin Mar. 2009.*
Office Action dated Jul. 24, 2012 issued to priority Japanese application No. 2008-196809.
Hurley, et al. "Quantitative Limulus Lysate Assay for Endotoxin and the Effect of Plasma," *Journal of Clinical Pathology*, vol. 44, No. 10, pp. 849-854, 1991.
Supplementary European Search Report, dated Feb. 28, 2012, issued to corresponding European patent application No. 09802945.7.
Obata, et al. "Early Detection of the *Limulus* Amebocyte Lysate Reaction Evoked by Endotoxins," *Analytical Biochemistry*, vol. 373, No. 2, pp. 281-286, Feb. 15, 2008.
International Search Report dated Aug. 25, 2009 and issued to international application PCT/JP2009/063405.

* cited by examiner

*Primary Examiner* — Bin Shen
(74) *Attorney, Agent, or Firm* — Knobbe, Martens, Olson & Bear LLP (57) ABSTRACT

Disclosed is a measurement method which can largely reduce the time required for the detection of a physiologically active substance derived from an organism (e.g., an endotoxin, β-D-glucan) or the determination of the concentration of the physiologically active substance by utilizing the reaction between the physiologically active substance and LAL. Also disclosed is a measurement apparatus utilizing the measurement method. An incident light from a light source is focused onto a sample and delivered to the sample to cause the bombardment with coagulin which is a final product of a protease cascade (i.e., a coagulin monomer) and an extremely fine aggregate which is produced by the aggregation of the coagulin monomers (i.e. a coagulin aggregate), thereby generating a scattered light. The scattered light is detected by a light-receiving element. The concentration of the endotoxin can be determined based on the initial rate of increase in the scattered light detected.

14 Claims, 6 Drawing Sheets

METHOD FOR MEASUREMENT OF PHYSIOLOGICALLY ACTIVE SUBSTANCE DERIVED FROM ORGANISM AND MEASUREMENT APPARATUS

CROSS-REFERENCE TO RELATED APPLICATIONS

This application is the U.S. National Phase under 35 U.S.C. §371 of International Application PCT/JP2009/063405, filed Jul. 28, 2009, which was published in a non-English language, which claims priority to JP Application No. 2008-196809, filed Jul. 30, 2008.

TECHNICAL FIELD

The present invention relates to a measurement method and a measurement apparatus for detecting a physiologically active substance derived from an organism, which has a property of gelating by a reaction with LAL, such as endotoxin or β-D-glucan, in a sample containing the physiologically active substance or for measuring the concentration of the physiologically active substance.

BACKGROUND ART

Endotoxin is a lipopolysaccharide present in a cell wall of a Gram-negative bacterium and is the most typical pyrogen. If a transfusion, a medicine for injection, or blood contaminated with the endotoxin is introduced into the human body, the endotoxin may induce severe side effects such as fever and shock. Therefore, it has been required that the above-mentioned medicine or the like be kept so as not to be contaminated with endotoxin.

By the way, a limulus amoebocyte lysate (hereinafter, also referred to as "LAL") contains serine proteases which are activated by endotoxin. In the case where LAL reacts with endotoxin, a coagulogen present in LAL is hydrolyzed into a coagulin by an enzyme cascade of the serine proteases activated depending on the amount of endotoxin, and the coagulin is associated with one another to form an insoluble gel. By using the characteristic of LAL, endotoxin can be detected with a high sensitivity.

Meanwhile, β-D-glucan is a polysaccharide which constitutes a cell membrane characteristic of a fungus. Measurement of β-D-glucan is effective, for example, for screening of infectious diseases due to a variety of fungi including not only fungi which are frequently observed in general clinical practices, such as Candida, Aspergillus, and Cryptococcus, but also rare fungi.

In measurement of β-D-glucan, by using the characteristic of a limulus amoebocyte lysate to coagulate (coagulate to form a gel) by β-D-glucan, β-D-glucan can be detected with a high sensitivity.

Various methods have been proposed as a method for detection or concentration measurement of a physiologically active substance derived from an organism (hereinafter, also referred to as a predetermined physiologically active substance) which can be detected by a limulus amoebocyte lysate, such as endotoxin or β-D-glucan. One of the methods is a semi-quantitative gelation method involving: leaving a mixture obtained by mixing a sample to be used for detection or concentration measurement of the predetermined physiologically active substance (hereinafter, also simply referred to as "measurement of the predetermined physiologically active substance") with LAL to stand still; inverting the container after a lapse of a predetermined time period; and judging whether the sample has gotten gelation or not based on the presence or absence of dipping of the sample to examine whether or not the sample contains endotoxin at a certain concentration or higher. As other examples of the method, there are also given a turbidimetric method involving analyzing a sample by measuring the time course of the turbidity of the sample caused by gel formation by a reaction between LAL and the predetermined physiologically active substance, a colorimetric method using a synthetic substrate which is hydrolyzed by an enzyme cascade to develop a color, and the like.

In the case where the predetermined physiologically active substance is measured by the above-mentioned turbidimetric method, a mixture of a measurement sample and LAL is produced in a dry-heat-sterilized glass measurement cell. Then, gelation of the mixture is optically measured from the outside. However, the turbidimetric method may require a very long period of time of for gelation of LAL particularly in a sample containing the predetermined physiologically active substance at a low concentration. To solve the problem, a method which can measure the predetermined physiologically active substance in a short period of time has been required. As examples of the method, there has been proposed a laser light scattering particle counting method or a stirring turbidimetric method capable of forming fine gel-particles by stirring a mixture of a measurement sample and LAL using a magnetic stirring bar, for example, and determining the presence of the predetermined physiologically active substance in the sample in a short period of time based on the intensity of laser light scattered by the fine gel-particles or based on the intensity of light transmitted through the mixture.

The above-mentioned various methods have been developed to reduce a detection time period or measurement time period of the predetermined physiologically active substance or to improve measurement sensitivity. However, all the methods have both advantages and disadvantages, and it has been desired to further improve the methods in terms of reduction in measurement time period, increase in the sensitivity, and elimination of interfering substances.

CITATION LIST

Patent Literature

[PTL 1] JP 2004-061314 A
[PTL 2] JP 10-293129 A
[PTL 3] WO 2008/038329 A1

SUMMARY OF INVENTION

Technical Problem

The present invention has been made in view of the above-mentioned problems, and an object of the present invention is to provide a measurement method which can detect a physiologically active substance derived from an organism or can reduce the measurement time period in measurement of the concentration, and a measurement apparatus using the method.

Solution to Problem

In the present invention, the inventors of the present invention have found that the measurement time period can be reduced by directly detecting coagulins themselves (coagulin monomers), which are final products of protease cascade, and extremely small associated products obtained by associating the coagulins (coagulin aggregates). The greatest characteristic of the method is detection of the concentration of the predetermined physiologically active substance or measurement of the concentration based on the increase rate of scattered light generated by irradiating a mixture of a sample for measurement of the predetermined physiologically active substance and LAL with light to cause the collision with particles by the mixture and detected in a light receiving element.

That is, the present invention is based on a novel finding which has resulted in intensive study by the inventor, that is, the finding that in the case where scattered light is generated by irradiating a mixture of the predetermined physiologically active substance and LAL with light to cause the collision with particles in the mixture, the increase rate of the scattered light detected by the light receiving element depends on the concentration of the predetermined physiologically active substance.

The present invention is based on the turbidimetric method using no special reagent as used in the colorimetric method, but as is the case with the colorimetric method, differentiation is applied to judgment by detecting scattered light of hydrophobic coagulin monomers changed from water-soluble protein coagulogens and oligomers obtained by aggregating some of the monomers, which are generated at an extremely early time of the gelation reaction of LAL with the predetermined physiologically active substance.

More specifically, the present invention is a method of measuring a physiologically active substance derived from an organism, which is used for detecting the physiologically active substance derived from an organism in a sample or measuring a concentration of the physiologically active substance, by reacting the physiologically active substance in the sample with LAL which is a limulus amoebocyte lysate, including:

emitting light into a mixture of the sample and the LAL and obtaining intensity of scattered light generated from the mixture by the incident light, after mixing of the sample and the LAL; and detecting the physiologically active substance in the sample or measuring the concentration of the physiologically active substance based on an increase rate of the scattered light intensity.

According to this method, it is possible to perform detection and concentration measurement of endotoxin or β-D-glucan by obtaining an increase rate of scattered light intensity in the case of emitting light into a mixture obtained by mixing endotoxin or β-D-glucan and LAL. Therefore, as is the case with the turbidimetric method, it is not necessary to wait for physical quantities to be obtained to exceed a predetermined threshold value, and detection or concentration measurement of the predetermined physiologically active substance can be performed at earlier time.

Further, in the present invention, the detecting the physiologically active substance in the sample or the measuring the concentration of the physiologically active substance may be performed based on the increase rate before a predetermined acute change in the increase rate of the scattered light intensity.

Here, in the present invention, generation of coagulin monomers and oligomers obtained by aggregating several monomers, which is caused at an extremely early time of the gelation reaction of LAL with the predetermined physiologically active substance, is detected by scattered light. As for the detection, the scattered light is considered to be mainly based on Rayleigh scattering because the scattered particles are very small and each have a size smaller than the wavelength of the incident light. In addition, as the particles grow thereafter, the scattered light is changed into one mainly based on Mie scattering.

Thus, when the particle system at the early time in a small region based on Rayleigh scattering is switched to that based on Mie scattering as the particles grow, a point where the increase rate of the scattered light is drastically changed is observed.

In response, in the present invention, the increase rate before a predetermined acute change in the increase rate of the scattered light intensity, i.e., the increase rate of the scattered light mainly based on Rayleigh scattering is detected. Therefore, it is possible to more accurately obtain the increase rate of scattered light from coagulin monomers and oligomers obtained by aggregating several monomers, generated at an extremely early time of the gelation reaction of LAL with the predetermined physiologically active substance. As a result, more accurate detection and concentration measurement of the predetermined physiologically active substance can be performed.

That is, in the present invention, weak scattered light from particles with an extremely small sizes is detected as described above, and hence power density of incident light is desirably as high as possible. Moreover, it has been newly found that detection can be favorably performed when the power density is 50 mW/mm$^2$ or more. Therefore, in the present invention, the power density of the light emitted into the mixture is desirably 50 mW/mm$^2$ or more. The output density may be adjusted by the power of the light source or by concentrating the incident light to more small diameter.

Further, in the present invention, a wavelength of the light entering the mixture may be 300 nm or more and 800 nm or less. That is, it has been found that the intensity of the scattered light based on Rayleigh scattering depends on the wavelength of the incident light, and a shorter wavelength is more advantageous for detection. On the other hand, an extremely short wavelength may negatively affect the functions of LAL and may cause a disadvantage in that a material such as an optical device must be changed into one suitable for such short wavelength. Under such circumstances, the use of a wavelength having the above-mentioned range can allow favorable measurement.

Further, in the present invention, there may be performed sampling and comparing of a plurality of scattered light intensities obtained in a predetermined period and determining of a minimum value of the intensities or a mode value of a histogram as scattered light intensity in the period, in obtaining the increase rate of the scattered light intensity.

As described above, in the present invention, the increase rate of the intensity of scattered light from particles having extremely small diameters, generated at an extremely early time of the gelation reaction of LAL with the predetermined physiologically active substance is measured. On the other hand, the mixture may contain contaminants such as undissolved reagents, remaining fine particles with a size of a micrometer level in production of the reagents, and small air bubbles generated by stirring of the sample. The number of the scattered light beams from such contaminants is small, but the scattered light is very strong. Therefore, weak signals scattered from coagulin monomers and small coagulin aggregates cannot be measured in some cases because the weak signals are overwhelmed by the scattered light from the contaminants.

On the other hand, in the present invention, a filter is used to determine, as a scattered light intensity in a predetermined period, a minimum value or a mode value of a histogram of values obtained by sampling and comparing a plurality of scattered light intensities obtained in the period. When the minimum value of the scattered light intensities sampled in the predetermined period or the mode value of the histogram is selected, the effect of the scattered light from the contaminants can be removed because the frequency itself of generation of strong scattered light from the contaminants is low.

Further, in the present invention, the mixture may be stirred in obtaining the scattered light intensity.

In the case where the mixture is left to stand without stirring, the sample finally gets gelation as is the case with the turbidimetric method to cause an increase in scattered light, but it may be difficult to detect the increase in scattered light generated from coagulin monomers and small coagulin aggregates at the early time of the reaction. Stirring of the mixture enables efficiently performing uniformization of the reaction, promotion of the reaction, and rapid conversion of generated coagulin monomers into oligomers. Moreover, stirring can suppress lowering of measurement accuracy due to an unwilling increase in the scattered light intensity, caused by stagnation of the undissolved reagents, remaining fine particles with a size of a micrometer level in production of the reagents, and small air bubbles in the mixture in a scattering region.

Further, in the present invention, a rate of stirring of the mixture may be 300 rpm or more and 3000 rpm or less.

Here, when the above-mentioned stirring rate is too small, the whole sample cannot be stirred. On the other hand, when the stirring rate is too large, measurement may be negatively affected because air bubbles may be easily mixed in a sample, or the process of aggregation of coagulin monomers may be inhibited. Therefore, when the stirring rate of the mixture is adjusted to the above-mentioned range, it is possible to successfully suppress mixing of fine particles with a size of a micrometer level and air bubbles and to avoid inhibition of the process of coagulin monomer aggregation.

Further, in the present invention, the physiologically active substance derived from an organism may be endotoxin or β-D-glucan.

In such case, detection or concentration measurement of endotoxin which is the most typical pyrogen can be carried out more accurately, and it is possible to suppress entry of a transfusion, a medicine for injection, or blood contaminated with endotoxin into the human body to induce side effects. Similarly, detection or concentration measurement of β-D-glucan can be carried out more accurately, and it is possible to carry out more accurate screening of infectious diseases due to a variety of fungi including not only fungi which are frequently observed in general clinical practices, such as Candida, Aspergillus, and Cryptococcus, but also rare fungi.

Further, the present invention may be an apparatus for measuring a physiologically active substance derived from an organism, which is used for detecting the physiologically active substance derived from an organism in a sample or measuring a concentration of the physiologically active substance by reacting the physiologically active substance in the sample with LAL which is a limulus amoebocyte lysate, including:

mixture retaining means which retains a mixture of the sample and the LAL so that light is capable of entering thereinto, and progresses the reaction between the physiologically active substance and the LAL;

light emitting means which emits light into the mixture in the mixture retaining means;

light receiving means which receives scattered light generated from the mixture by the incident light and converts the light into an electrical signal; and derivation means which derives the concentration of the physiologically active substance in the sample based on an increase rate of intensity of the scattered light obtained from the electrical signal converted by the light receiving means.

According to the measurement apparatus, it is possible to detect the predetermined physiologically active substance such as endotoxin or β-D-glucan or to measure the concentration of the substance in a shorter period of time.

Further, the derivation means may derive the concentration of the physiologically active substance in the sample based on the increase rate after mixing of the sample and the LAL by the mixture retaining means and before a predetermined acute change in the increase rate. In this manner, the increase rate of scattered light from coagulin monomers and oligomers obtained by aggregating several monomers can be obtained more accurately, and it is possible to more accurately detect the predetermined physiologically active substance and to more accurately measure the concentration of the substance.

Further, in such case, the power density of the light emitted by the light emitting means may be 50 mW/mm$^2$ or more. In addition, the wavelength of the light emitted by the light emitting means may be 300 nm or more and 800 nm or less. In this manner, more efficient and successful measurement can be realized.

Further, in the present invention, there may be further provided a minimum value filter which outputs a minimum value of values obtained by sampling and comparing a plurality of electrical signals converted by the light receiving means in a predetermined period or a mode filter which outputs a mode value of a histogram. In this manner, the effect of scattered light from a variety of contaminants in the mixture can be removed, and more accurate detection or concentration measurement of the predetermined physiologically active substance can be performed.

Further, the mixture retaining means may have stirring means which stirs the mixture. In such case, the rate of stirring of the mixture by the stirring means is desirably 300 rpm or more and 3000 rpm or less. In this manner, it is possible to suppress lowering of measurement accuracy due to an unwilling increase in the scattered light intensity caused by stagnation of the contaminants in a scattering region and to avoid inhibition of the process of aggregation of the coagulin monomers.

The physiologically active substance derived from an organism may be endotoxin or β-D-glucan.

It should be noted that the above-mentioned means for solving the problems of the present invention may be combined to a maximum extent.

Advantageous Effects of Invention

According to the present invention, it is possible to reduce the measurement time period in detection or concentration measurement of physiologically active substance derived from an organism such as endotoxin or β-D-glucan by using a reaction between the physiologically active substance and LAL.

DESCRIPTION OF EMBODIMENTS

Figure 6:
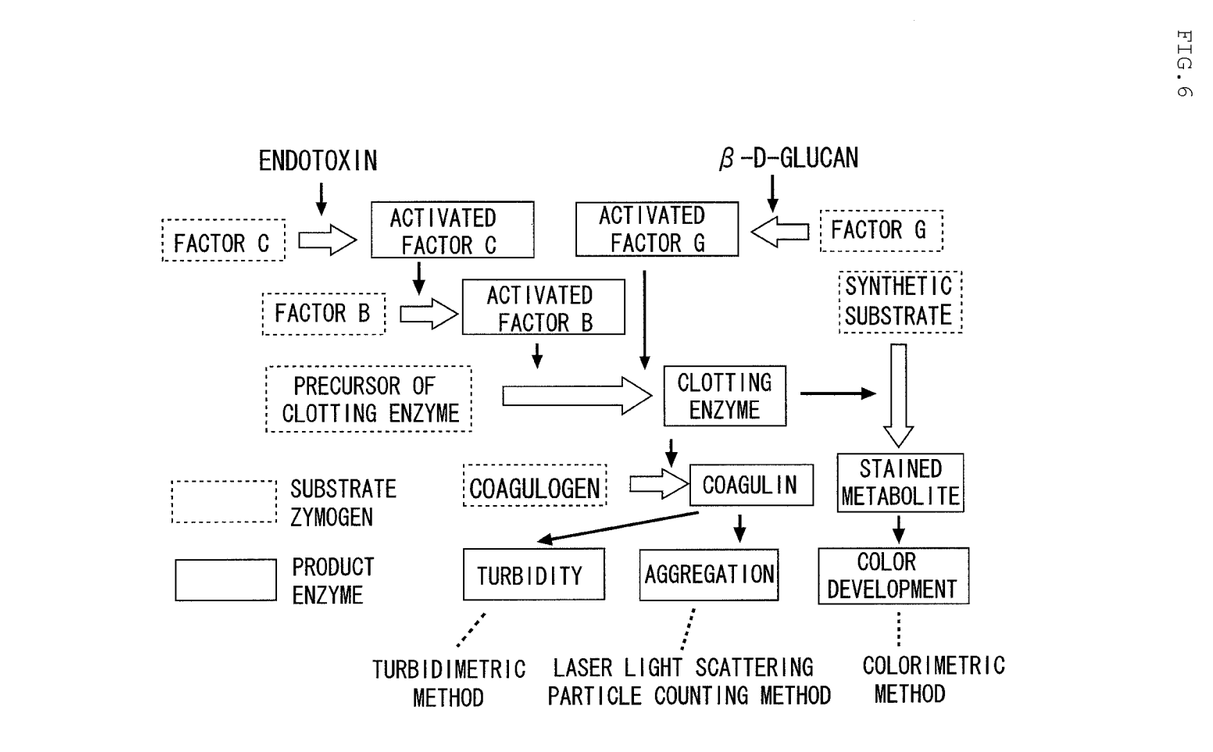
FIG. 6 A schematic diagram illustrating a gelation process of LAL by endotoxin or β-D-glucan and a method of detecting them.

The process of forming a gel by a reaction between LAL and endotoxin has been studied well. That is, as illustrated in FIG. 6, when endotoxin is bound to a serine protease, i.e., factor C in LAL, the factor C is activated to become activated factor C. The activated factor C hydrolyzes and activates another serine protease, i.e., factor B in LAL, and then the factor B is activated to become activated factor B. The activated factor B immediately hydrolyzes a precursor of clotting enzyme in LAL to form clotting enzyme, and further the clotting enzyme hydrolyzes a coagulogen in LAL to generate coagulin. Thus, the generated coagulin are then associated with each other to further form an insoluble gel, and the whole LAL is involved in the formation to turn into a gel.

In addition, similarly, when β-D-glucan is bound to factor G in LAL, the factor G is activated to become activated factor G. The activated factor G hydrolyzes a precursor of clotting enzyme in LAL to produce clotting enzyme. As a result, as is the case with the reaction between endotoxin and LAL, coagulin are generated, and the generated coagulin are associated with each other to further generate an insoluble gel.

The series of reactions as described above are similar to the process of forming a fibrin gel via serine proteases such as Christmas factor or, thrombin present in mammals. Such enzyme cascade reactions have a very strong amplification effect because even a very small amount of an activation factor activates the subsequent cascade in a chain reaction. Therefore, according to a method of measuring a predetermined physiologically active substance using LAL, it is possible to detect a very small amount (sub-pg/mL order) of the predetermined physiologically active substance.

Figure 1:
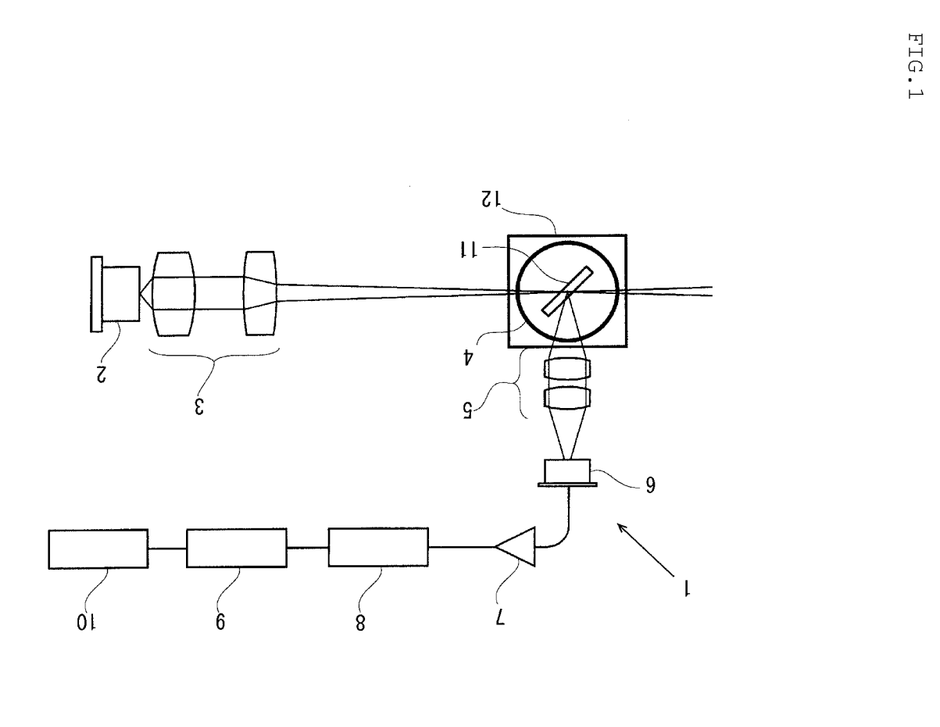
FIG. 1 A diagram illustrating a schematic configuration of a measurement system for a predetermined physiologically active substance in Examples of the present invention.

Examples of a measurement method which can quantify the predetermined physiologically active substance include the turbidimetric method and the laser light scattering particle counting method, as described above. As illustrated in FIG. 1, in such measurement methods, measurement can be performed with a high sensitivity by detecting association products of coagulin formed by the enzyme cascade reactions in LAL as the turbidity of a sample in the former method or as fine gel-particles formed in the system in the latter method.

In particular, in the laser light scattering particle counting method, fine gel-particles formed in the system are directly measured, and hence the method is more sensitive than the turbidimetric method. In addition, gel formation can be detected in a short period of time compared with the turbidimetric method because in general, a sample containing LAL and an analyte is forcibly stirred.

In addition, another method of measuring endotoxin further includes a colorimetric method. As illustrated in FIG. 6, the method does not measure the turbidity of a sample caused by a coagulin gel although the method is based on the enzyme cascade reactions in LAL. The method utilizes such as synthetic substrate that is hydrolyzed by clotting enzyme to develop a color, and is performed by measuring absorbance changes caused by a reaction between an analyte and LAL containing the synthetic substrate. In the colorimetric method, the concentration of a chromogenic substance formed in the system is measured, and hence a lower concentration predetermined physiologically active substance can be measured in a shorter period of time compared with the turbidimetric method or laser light scattering particle counting method, in both of which gel formation in a sample is measured.

The turbidimetric method is evaluated to be convenient in actual use because a special reagent is not required unlike the colorimetric method and the concentration range of the predetermined physiologically active substance able to be measured is wide. However, the turbidimetric method has a problem in that it takes a very long period of time to measure a low concentration predetermined physiologically active substance. This is because the turbidimetric method does not focus on the amount of the generated coagulins themselves which are final products of the protease cascade but focus on the process of a decrease in light transmittance due to a gel formed by associating the coagulins.

That is, it is necessary to wait for formation of a gel in order to detect the predetermined physiologically active substance by the turbidimetric Method because gelation is not caused until the concentration of coagulins reaches a certain level. Therefore, in the case where the concentration of the physiologically active substance is high, the measurement time period is reduced because a sufficient concentration of coagulins are rapidly generated to initiate gelation, while in the case where the concentration of the physiologically active substance is low, it takes a long period of time to reach the coagulin concentration required for gelation, resulting in increasing the measurement time period.

In addition, the laser light scattering particle counting method has been developed by improving the turbidimetric method in that a sample is stirred and in that particles are detected by laser instead of gelation, and the laser light scattering particle counting method can drastically reduce the measurement time period compared with the turbidimetric method. However, the observed gel particles are relatively large (several micrometers or more), and the reduction degree of the measurement time period is lower than that of the colorimetric method. The turbidimetric method and the laser light, scattering particle counting method are common in that the time when a physical quantity exceeds a certain threshold value is recorded as a reaction starting point (hereinafter, the method is referred to as threshold method for convenience) although the physical quantities observed in both the methods are different.

On the other hand, the above-mentioned colorimetric method detects color development of a stained metabolite of a synthetic substrate corresponding to a final product of the protease cascade, and hence the progression degree of color development in a predetermined time period (increase rate-differential) may be detected. Therefore, it is not necessary to wait for the occurrence of gelation, and the measurement time period can be reduced (hereinafter, the method is called differential method). However, the method has problems such as the need of a special reagent and the narrow range of concentration able to be measured.

In the present invention, the following method has been completed to solve the disadvantages in the above-mentioned various methods. That is, light from a light source is focused onto, and irradiated to, the mixture of the predetermined physiologically active substance and LAL to cause the collision with coagulins themselves which are final products of the protease cascade (coagulin monomers) and extremely small associated products obtained by associating the monomers (coagulin aggregates), thereby generating scattered light. Then, the increase rate of scattered light detected by a light receiving element is calculated to measure the concentration of the predetermined physiologically active substance, which highly correlates with the increase rate.

As described above, the present invention is based on the turbidimetric method which detects the LAL gelation itself, and hence it is possible to detect a low concentration predetermined physiologically active substance using a usual LAL reagent in a short period of time without using a special reagent. Moreover, in the process of the concentration measurement, the differential method which detects the increase rate of the scattered light intensity in a predetermined time period is employed. Therefore, the measurement time period can be reduced because it is not necessary to wait for the occurrence of gelation as is the case with the colorimetric method.

<Focusing of Incident Light>

Laser or high-intensity LED is used as the light source of the present invention, and the light is focused by a lens and irradiated to the mixture. Thus, the light energy of the incident light can be concentrated to the irradiated part, and hence it is possible to generate and detect scattered light with sufficient intensity from extremely fine particles such as coagulin monomers and small coagulin aggregates.

On the other hand, in the case where wide parallel light such as a laser pointer is emitted into the sample, the light energy cannot be concentrated and irradiated to one point in the sample, and hence scattered light with sufficient intensity cannot be obtained from extremely fine particles such as coagulin monomers and small coagulin aggregates. Such method is within a range of the conventional turbidimetric method because laser is merely substituted for the light source.

<Stirring of Sample>

Further, in the present invention, the sample is stirred by a stir bar incorporated into a measurement container, and stirring of the sample enables efficiently performing uniformization of the reaction, promotion of the reaction, and rapid conversion of generated coagulin monomers into oligomers. In the case where the sample is left to stand without stirring, it may be difficult to accurately detect an increase in scattered light from coagulin monomers and small coagulin aggregates at the early time of the reaction although an increase in scattered light is observed because the sample finally gets gelation as is the case with the turbidimetric method.

<Removal of Noise (Filtering)>

Further, the sample contains undissolved reagents, remaining fine particles with a size of a micrometer level in production of the reagents, and small air bubbles generated by stirring of the sample. Weak signals scattered from coagulin monomers and small coagulin aggregates cannot be measured without further treatments because, although the number of the contaminants is small, the contaminants generate scattered light which is very strong, and hence the weak signals are overwhelmed by the scattered light of the contaminants.

In the present invention, a plurality of scattered light intensities obtained in a predetermined period are sampled and compared, and the effects of contaminants are eliminated by using a filter which outputs the minimum value of the values or the mode value of a histogram as the scattered light intensity in the period, to thereby obtain weak scattered light of a target substance.

<Combination of the Present Invention and Threshold Method>

As described above, the present invention focuses attention on that the rate of the temporal change in the obtained weak scattered light generated from an measuring target becomes larger as the concentration of endotoxin used increases, and the rate becomes smaller as the concentration decreases. Therefore, even in the case of a sample containing a low concentration of endotoxin, the concentration can be quantitatively measured in a short period of time without waiting for appearance of aggregated fine particles or gelation. In the present invention, this is achieved by the effect of utilizing differential method as is the case with the colorimetric method.

However, in the case where the concentration of the predetermined physiologically active substance is very high, coagulogen polymers with a size of a micrometer level may be formed by associating target substances such as coagulogen monomers and coagulogen oligomers before the increase rate of weak scattered light from the substances is sufficiently observed. In such case, the increase rate of weak scattered light generated from the measuring target may not be calculated. Therefore, in such case, the threshold method for calculating the concentration at the time when the scattered light intensity exceeds a certain level may be employed. It is possible to simultaneously measure a wide range of concentrations by combining the advantages of the differential method and threshold method depending on different cases as described above.

Hereinafter, best modes for carrying out this invention are described illustratively in detail. However, the present invention is not limited to the following modes.

FIG. 1 illustrates a schematic configuration of the measurement system 1 for the predetermined physiologically active substance in this mode. Laser or high-intensity LED is used as a light source 2 used in the measurement system 1. Light emitted from the light source 2 is focused by the optical system for incident light 3 and the focused light enters the sample cell 4. The sample cell 4 retains a mixture of a sample which requires measurement of the predetermined physiologically active substance and an LAL reagent. The light which has entered the sample cell 4 is scattered by particles (measuring targets such as coagulogen monomers and coagulogen oligomers) in the mixture.

The optical system for outgoing light 5 is arranged laterally to the incident light axis in the sample cell 4. Further, a light receiving element 6 which receives scattered light that has been scattered by particles in the mixture in the sample cell 4 and has been focused by the optical system for outgoing light 5, and which converts the light into an electrical signal is arranged on an extension of the optical axis of the optical system for outgoing light 5. The light receiving element 6 is electrically connected to an amplifier circuit 7 which amplifies the electrical signal obtained by photoelectric conversion in the light receiving element 6. The measurement system is further equipped with a filter 8 for removing noises from electrical signals amplified by the amplifier circuit 7, a calculation apparatus 9 which calculates the increase rate of scattered light based on the electrical signals after removal of the noises and further derives the concentration of the predetermined physiologically active substance, and a display 10 which displays the results.

In the measurement system 1, the measuring target is small, and hence the scattered light from the measuring target is considered to be generated by Rayleigh scattering. In such case, the scattered light intensity ks is represented by the following expression.

$$k_s = \frac{2\pi^6}{3}n\left(\frac{m^2-1}{m^2+2}\right)^2 \frac{d^5}{\lambda^4} \qquad \text{[Math. 1]}$$

Here, n represents the number of particles, d represents a particle size, m represents a reflection coefficient, and λ, represents a wavelength of incident light. Therefore, measurement can be more advantageously performed when the wavelength in the light source 2 is shorter. However, LAL contains a high concentration of proteins, and hence an extremely short wavelength of light is impractical because the light has harmful, effects on the function of LAL and requires a special material for optically transmitting such short wavelength of light.

Therefore, the wavelength of the incident light is not required to be particularly limited but is desirably within a range of 250 nm to 1200 nm. The wavelength is more desirably within a range of 300 nm to 800 nm. If the wavelength of the incident light is within the range of 300 nm to 800 nm, scattered light can be obtained quite efficiently. Moreover, the light has no effects on the function of LAL and enables use of optical parts made of a general material. Further, in the case where the light source is focused onto the sample, scattered light from fine particles (measuring targets such as coagulogen monomers and coagulogen oligomers) in the mixture is required to have sufficient intensity. Therefore, the beam width (beam diameter) of light entering the sample cell 4 is preferably 3 mm or less, more preferably 1 mm or less. If the power density of the incident light of 50 mW/mm² or more can be achieved using a general light source which generates incident light with a wavelength in a range of 250 nm to 1200 nm, scattered light having sufficient intensity can be obtained.

Next, the light receiving element 6 which receives the scattered light is required to detect weak scattered light with low noise. Therefore, as the light receiving element 6, there area given a photodiode, a phototransistor, and an array including many of them, and a photomultiplier.

Further, in addition to the above-mentioned elements, a line sensor or an area sensor using charge-coupled device (CCD) or complementary metal oxide semiconductor (C-MOS) may be used. The intensity of the scattered light obtained by the light receiving element 6 is extremely weak compared with the intensity of scattered light obtained from fine particles with a size of a micrometer level, and hence, in general, it is necessary to amplify the electrical signal using at least one amplifier circuit 7 using a resistor or an operational amplifier.

Next, as the filter 8 for removing the effects of fine particles which contaminate a sample or a reagent, there are given: 1) a minimum value filter which outputs the minimum value of values obtained by sampling and comparing some scattered light intensities in a restricted time period (in predetermined period) or a mode filter which outputs the mode value of a histogram; 2) a frequency filter for removing scattered light from contaminants, which is generated infrequently compared with the scattered light from a target substance, in an electronic circuit; and 3) a digital filter which obtains temporal potential changes and removes contaminants digitally. When at least one of the filters is used, it is possible to eliminate the effects of the contaminants and to obtain weak scattered light of the objective substance.

Further, the weak scattered light from the measuring target, which has been passed through the filter 8, may have a large value at the time of measurement starting because of the amplifier circuit 7 in the previous stage. Therefore, the value may be removed as a baseline, and the resultant value may be used for an analysis after appropriately amplifying the value.

Next, means for calculating the concentration of the predetermined physiologically active substance based on the intensity of the weak scattered light obtained from the measuring target in the calculation apparatus 9 is shown below. That is, dilution series of the predetermined physiologically active substances in known concentrations are prepared, and 1) the increase rate of scattered light intensity, which is obtained as a slope when the time and scattered light intensity are plotted on the horizontal axis and the vertical axis, respectively (differential method), and 2) the time when a difference obtained by subtracting the initial scattered light intensity from the scattered light intensity at each time exceeds a predetermined threshold value (threshold method) are calculated for the respective samples. Then, a relational expression (calibration curve) of the concentration of the predetermined physiologically active substance and the resultant values is calculated, and a value obtained for a sample containing an unknown concentration of the predetermined physiologically active substance is applied to any one of or both of the calibration curve obtained by the differential method and the calibration curve obtained by the threshold method. As a result, the concentration of the predetermined physiologically active substance can be measured.

In addition, in order to efficiently generate coagulin monomers and small coagulin aggregates, the sample is desirably stirred. Therefore, in this mode, the sample cell 4 is equipped with a magnetic stir bar (stir bar) 11 which rotates by being applied with electromagnetic force from outside for stirring the mixture as a sample, and the measurement system 1 outside the sample cell 4 is equipped with a magnetic stirrer 12. The stirrers enable adjustment of whether or not to perform stirring, and the stirring rate.

Here, if the stirring rate is too low, the whole sample cannot be stirred. On the other hand, if the rate is too high, the measurement may be adversely affected because air bubbles may be easily mixed in the sample, or the process of aggregation of the coagulin monomers is inhibited. Therefore, the stirring rate is preferably in a range of 100 rpm to 5000 rpm, more preferably in a range of 300 rpm to 3000 rpm. In the case where the stirring rate is 2000 rpm or more, suppression of the aggregation may be observed, while in the case where the stirring rate is 500 rpm or less, the coagulin aggregation may be observed only on the lower side of the sample because the sample is insufficiently stirred. Moreover, the stirring has an effect of preventing fine particles larger than the measuring targets such as coagulin monomers and small coagulin aggregates (which are air bubbles, contaminants contained in the sample from the beginning, or the like) from remaining on the beam of the light source, and hence the effects of variation in the data or apparent increase in the scattered light can be suppressed.

Production Example 1

A stainless stir bar (φ1 mm, length 5 mm) was placed in a glass container (outer diameter φ7 mm, length 50 mm, hereinafter, abbreviated as cuvette), and the opening section of the cuvette was covered with aluminum foil. Some of the covered cuvettes were collectively further covered with the aluminum foil and subjected to heat treatment at 250° C. for 3 hours to sterilize the glass containers (dry-heat sterilization). According to this procedure, endotoxin adhering to the containers were thermally decomposed and inactivated.

Example 1

An illumination optical system capable of focusing and irradiating laser beam (diameter of input port into sample is 0.2 mm) was produced using a semiconductor laser (power 10 mW, wavelength 655 nm) in appropriate combination of lenses. In this case, the power density of incident light is about 80 mW/mm$^2$. A sample containing 0.01 EU/mL endotoxin was mixed with LAL (Limulus ES-II Single Test Wako: manufactured by Wako Pure Chemical Industries, Ltd.), and then the mixture was charged in the cuvettes produced in Production Example 1. The cuvettes were set in a holder part capable of rotating the stainless stir bar 11 in the sample by the magnetic stirrer 12 as illustrated in FIG. 1 to stir the mixture. In this example, the cuvettes were used as the sample cells 4.

Stirring of the sample was performed at 1000 rpm. It should be noted that the holder part was heat-retained at 37° C. to progress the gelation reaction of LAL. The sample containing the LAL reagent and endotoxin was irradiated with incident light from the above-mentioned light source 2, and laterally scattered light generated from the coagulin monomers and small coagulin aggregates generated in the sample was received by the light receiving element 6 placed in the direction of 90 degrees with respect to the light axis of the light source. A photodiode was used as the light receiving element 6 of the laterally scattered light.

The received scattered light components include, in addition to weak scattered light generated from the coagulin monomers and small coagulin aggregates, strong scattered light generated from fine particles in the sample (such as undissolved reagents, fine particles contained in the reagents from the beginning, and small air bubbles). Therefore, the scattered light generated from the contaminants was removed by utilizing a minimum value filter as the filter 8, and time-series changes in the scattered light were recorded. The minimum value filter was used to measure the minimum value of 25 data items, which are obtained by repeating a process including appropriately amplifying the light potential received by the light receiving element 6 in the amplifier circuit 7 and performing analog-digital conversion (10 bits), 25 times every 20 milliseconds. Here, the 20 milliseconds correspond to the predetermined period in this example.

Example 2

An optical system (diameter of input port into sample is 3.0 mm) capable of irradiating laser light as parallel light like a laser pointer was produced using a semiconductor laser (power 10 mW; wavelength 655 nm) in appropriate combination of lenses. The differences from Example 1 are only the conditions of the light source optical system, and as for the other conditions, the same treatment as in Example 1 was performed to record time-series changes in the scattered light. It should be noted that, in this case, the power density of incident light is about 0.35 mW/mm$^2$.

Figure 2:
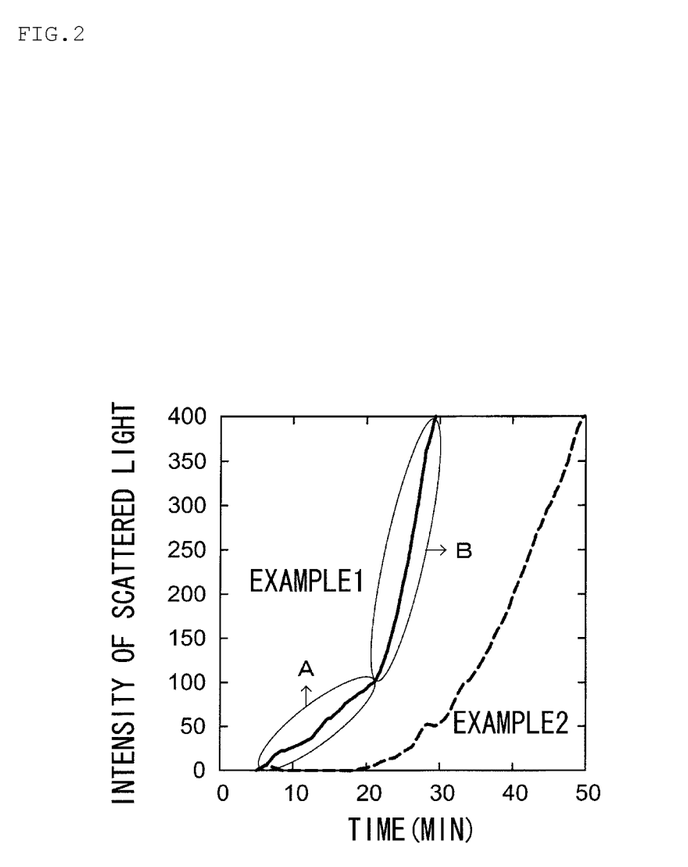
FIG. 2 A graph showing temporal changes in intensities of scattered light from mixtures obtained in Examples 1 and 2 of the present invention.

FIG. 2 shows the results of Examples 1 and 2. In FIG. 2, the horizontal axis represents the time (min), and the vertical axis represents the scattered light intensity obtained from the power of the photodiode. In Example 1, as shown in the part A surrounded by the ellipse in the figure, there is a phase where the scattered light increases form the early time of the reaction, and then the phase is changed to the phase B with a larger slope via the folding point. On the other hand, in Example 2, the phase A is little observed, and the subsequent phase B is mainly observed. The measurement conditions including the concentration of endotoxin used in Examples 1 and 2 are the same except for the measurement conditions of the light source 2. Therefore, in Example 2, it is considered that changes progressing in the sample cannot be detected because sufficient scattered light cannot be obtained from the fine particles. It should be noted that the folding point in the curve of Example 1 corresponds to the point when the predetermined acute change occurs.

As described above, in order to obtain scattered light from detection targets such as coagulin monomers and small coagulin aggregates, it is necessary to ensure sufficient power density by sufficiently focusing the light source 2 such as high-power laser onto a sample and irradiating the sample with the light.

Example 3

Under the same conditions as in Example 1 but without stirring of a sample, time-series changes in the scattered light were recorded. As a result, even in the case where stirring is not performed, coagulin monomers and small coagulin aggregates were found to increase over time. However, there was a lot of variation in the obtained data. Moreover, in the case where particles larger than target fine particles were present on the beam of the light source 2, the particles stay at the same position for a long period of time, and hence very strong apparent scattered light was observed in some cases even when a minimum value filtering treatment or the like was performed for the data. In such case, it was difficult to accurately evaluate a phenomenon where weak scattered light increases. On the other hand, in the case where the sample was stirred, evaluation was able to be performed accurately because the large particles did not stay on the beam and were rapidly deviated.

Example 4

A treatment was performed under the same conditions as in Example 1 using the light source 2 and optical system for incident light 3 used in Example 1 except that the scattered light filtering treatment was performed using a mean filter, and time-series changes in the scattered light were recorded. The mean filter was used to output a mean value of 25 data items, which are obtained by repeating a process including appropriately amplifying the light potential received by the light receiving element 6 in the amplifier circuit 7 and performing analog-digital conversion (10 bits), 25 times every 20 milliseconds.

As a result, the resultant data was greatly affected by the scattered light of the particles larger than the target fine particles, and it was difficult to accurately evaluate the phenomenon where weak scattered light was increasing. As the particles larger than the target fine particles, such as coagulin monomers and small coagulin aggregates, there are given small air bubbles and undissolved reagents mixed into the mixture, and cell fragments which are not removed in a process of producing the reagent. The particles appear differently from mixture to mixture, and hence it is considered that the particles cannot be removed appropriately as long as the mean-value method is employed.

Next, in order to test the general filter performances, the performances of the following filters 8 were examined using a simulated sample of an measuring target, i.e., a mixture of a neutral fat (0.0002% Intralipid) and polystyrene latex particles (φ1 μm, percentage by weight 0.0025%). The filters 8 include: 1) a median filter which outputs the 13th value of 25 data items arranged in descending order, the 25 data items being obtained by repeating a process including appropriately amplifying a light potential received by the light receiving element 6 in the amplifier circuit 7 and performing analog-digital conversion (10 bits), 25 times every 20 milliseconds; 2) a mean filter which outputs the mean value of the 25 data items; 3) a minimum value filter which outputs the minimum value of the 25 data items; and 4) a maximum value filter which outputs the maximum value of the 25 data items. Values were output every 6 seconds through the filters, and mean values (the numeric values are voltage values after amplification in the amplifier circuit 7) and standard deviations of the numeric values obtained by the treatments of the filters were calculated based on 50 data items in total obtained in 5 minutes, and the results shown in Table 1 were obtained.

TABLE 1

| Type of filter | Median filter | Mean filter | Minimum value filter | Maximum value filter |
| --- | --- | --- | --- | --- |
| Mean of output (voltage) | 2.64 | 2.80 | 2.17 | 4.78 |
| Standard deviation | 0.15 | 0.17 | 0.06 | 0.32 |

The results were obtained for the simulated sample, but it is obvious that the minimum value filter is most suitable for measuring small scattered light of a target substance because of the following reasons. 1) The mean value is lower than the results of the other filters, but this is because the filter mainly outputs scattered light of the target substance with lower intensity. 2) The standard deviation is smaller than the results of the other filters, which indicates that the filter is hardly affected by the scattered light of larger fine particles contaminating the sample. On the other hand, the maximum value filter outputs a large mean value and a large standard deviation because the filter does not output the scattered light of the target substance but mainly outputs signals of fine particles contaminating the sample. Meanwhile, the mean filter outputs an intermediate value of the value of the minimum value filter and the value of the maximum value filter because the filter outputs a mean value of both weak scattered light of the target substance and scattered light of fine particles contaminating the sample. In addition, the median filter provides the results similar to those of the mean filter and does not demonstrate superior performance.

It should be noted that, in the case where the number of sampled data items is small, the above-mentioned minimum value filter is considered to be effective. However, in the case of performing continuous sampling, a histogram can be produced because the number of data items is large. In such case, the mode filter which outputs the most frequent value (a site where a peak is present) in the histogram may be used to eliminate the effect of the scattered light of larger fine particles contaminating the sample.

In addition, as a modified example of the minimum value filter, a filter which outputs a smaller value of a specific order of the sampled data and a mean value thereof may be employed. For example, a filter which outputs a mean value of 5 data items 6 smaller values (excluding the smallest value) of 25 data items obtained and sorted is effectively used.

Example 5

Figure 3:
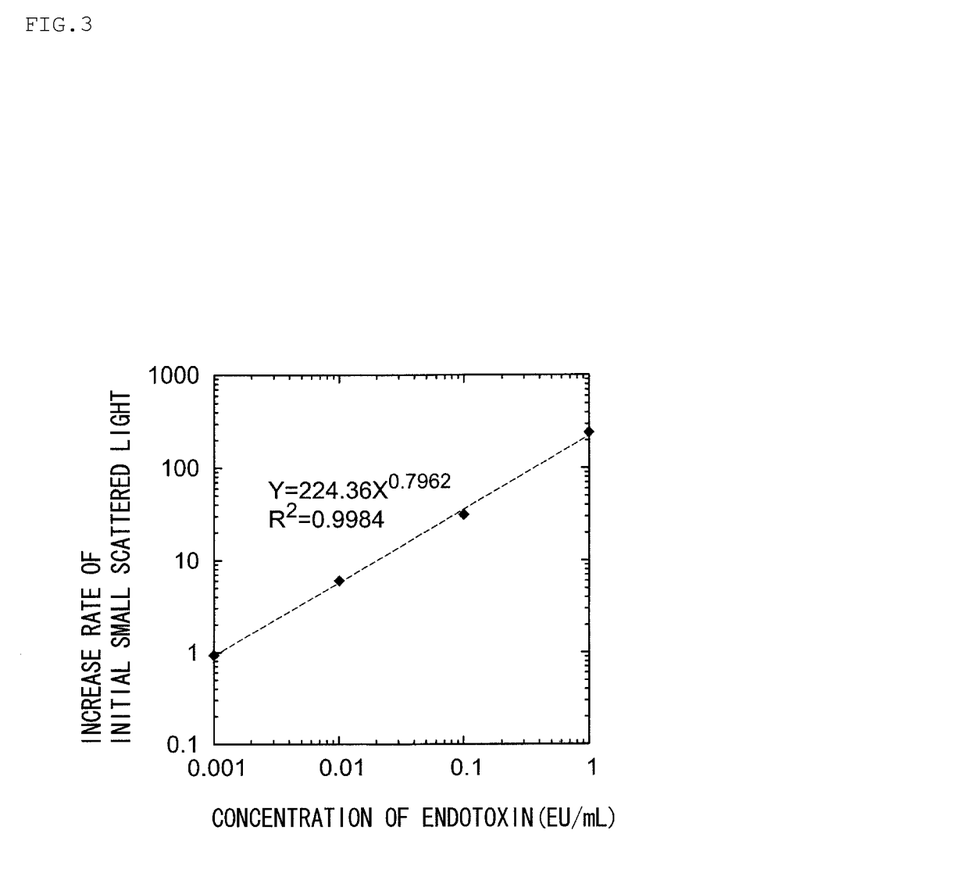
FIG. 3 A double logarithmic graph obtained by plotting a relationship between a concentration of endotoxin and an increase rate of initial scattered light intensity in Example 5 of the present invention.

Endotoxin dilution series were prepared at a variety of concentrations by the method shown in Example 1 to examine a relationship between the concentration of endotoxin and the increase rate of initial scattered light generated from coagulin monomers and small coagulin aggregates. As a result, it was found that, the increase rate became lower as the concentration of endotoxin became lower, and the increase rate became higher as the concentration became higher. When the relationship between the concentration of endotoxin and the increase rate of the initial scattered light was plotted in a double logarithmic graph, a linear relation was obtained as shown in FIG. 3. The horizontal axis represents the concentration of endotoxin (EU/mL), and the vertical axis represents the increase rate of initial small scattered light (the slope of the rise curve of initial scattered light).

Example 6

Figure 4:
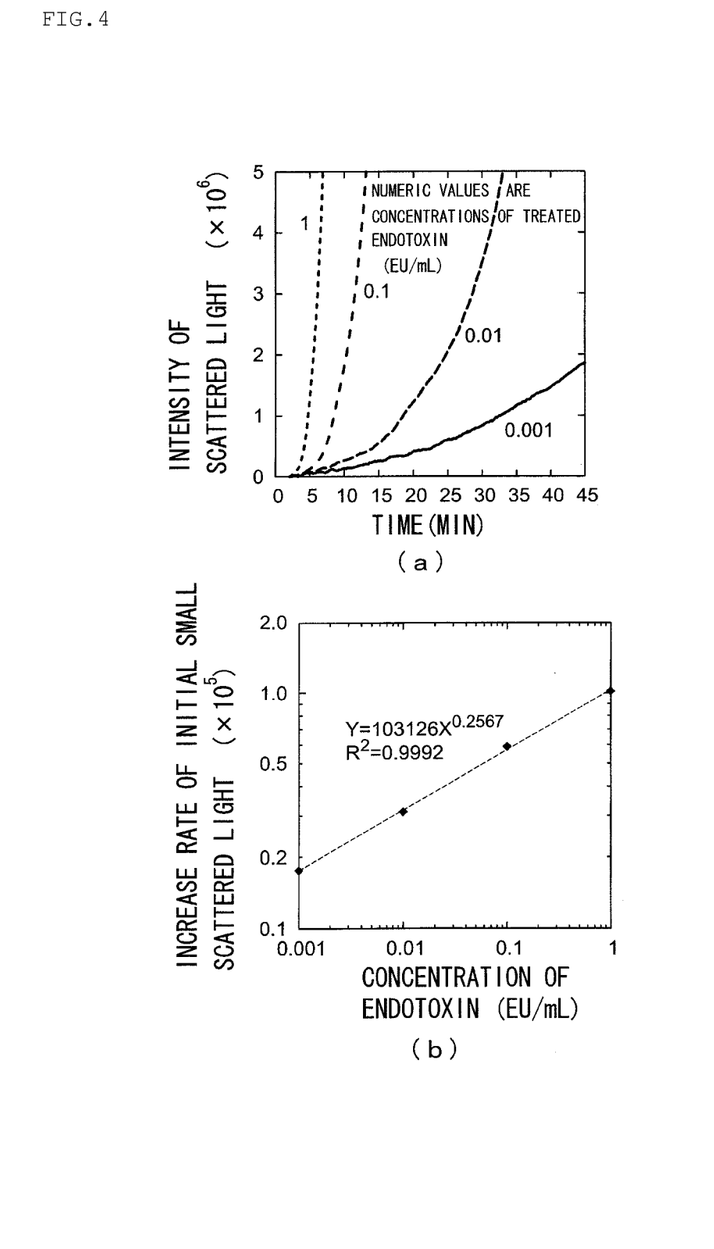
FIGS. 4A and 4B Graphs showing temporal changes in scattered light intensity (FIG. 4A) and a relationship between a concentration of endotoxin and an increase rate of initial scattered light intensity (FIG. 4B) in Example 6 of the present invention.

An apparatus was produced in the same way as in Example 1 except that a CCD area sensor was used instead of the photodiode used as the scattered light receiving element 6, to thereby, similarly to Example 5, examine a relationship between the concentration of endotoxin and the increase rate of initial scattered light. FIG. 4(*b*) shows the results. In FIG. 4(*b*), the horizontal axis represents the concentration of endotoxin (EU/mL), and the vertical axis represents the increase rate of initial small scattered light (the slope of the rise curve of initial scattered light).

FIG. 4(*a*) further shows the temporal changes in the intensity of scattered light. In FIG. 4(*a*), the horizontal axis represents the time (min), and the vertical axis represents the scattered light intensity obtained based on the output of the CCD area sensor. The graph also shows that, also in the case of using the CCD area sensor, the initial scattered light increases linearly like the phase A in FIG. 2 and further changes to the phase of a larger increase rate (the phase shown by the ellipse B in FIG. 2) via the folding point.

Example 7

Figure 5:
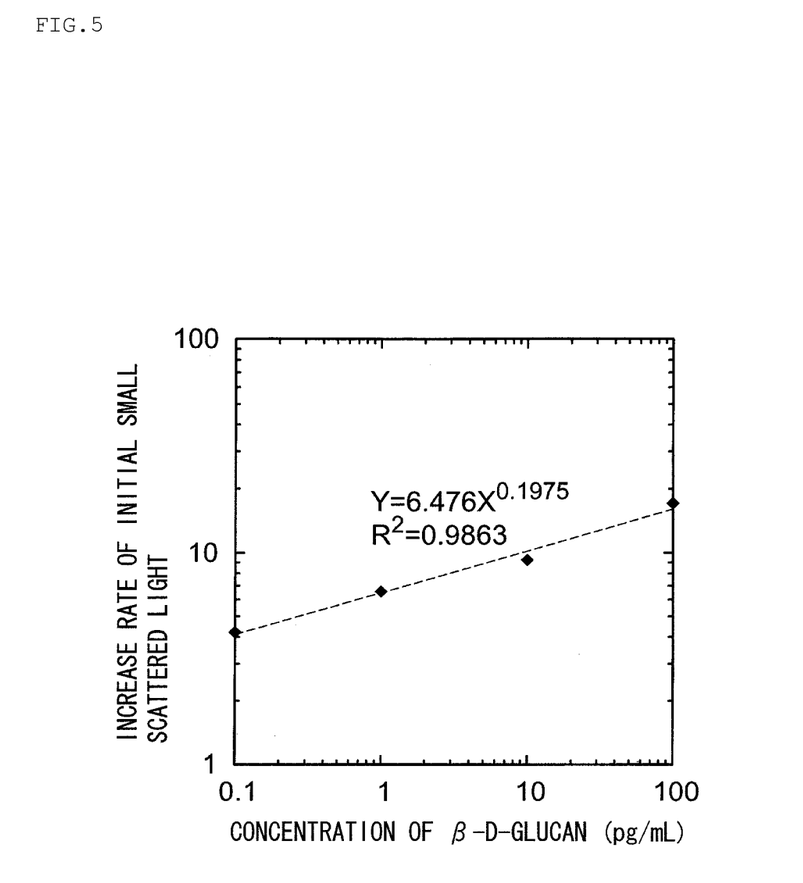
FIG. 5 A double logarithmic graph obtained by plotting a relationship between a concentration of β-D-glucan and an increase rate of initial scattered light intensity in Example 7 of the present invention.

An examination was performed in the same way as in Example 1 using β-D-glucan instead of endotoxin. β-Glucan Test Wako (manufactured by Wako Pure Chemical Industries, Ltd.) was used as the LAL reagent. β-D-glucan dilution series were prepared at a variety of concentrations to examine a relationship between the concentration of β-D-glucan and the increase rate of initial scattered light generated from coagulin monomers and small coagulin aggregates. As the result, it was found that the increase rate became lower as the concentration of β-D-glucan became lower, and the increase rate became higher as the concentration became higher. When the relationship between the concentration of β-D-glucan and the increase rate of the initial scattered light was plotted in a double logarithmic graph, a linear relation was obtained as shown in FIG. 5. In FIG. 5, the horizontal axis represents the concentration of β-D-glucan (pg/mL), and the vertical axis represents the increase rate of initial small scattered light (the slope of the rise curve of initial scattered light).

Here, a measurement apparatus including the entire of the measurement system 1 for the predetermined physiologically active substance as shown in FIG. 1 may be configurated. In such case, the above-mentioned measurement can be automatically performed only by introducing a mixture of a sample containing the predetermined physiologically active substance and LAL into the sample cell 4 and providing direction of measurement starting. Moreover, in the calculation apparatus 9, the concentration of the predetermined physiologically active substance may be calculated based on the calibration curves obtained in FIGS. 3, 4, and 5 and the increase rate obtained from scattered light from the mixture, and the results may be automatically displayed by the display 10.

In such case, the sample cell 4 corresponds to mixture retaining unit, the light source 2 and optical system for incident light 3 correspond to light emitting unit, the optical system for outgoing light 5 and light receiving element 6 correspond to light receiving unit, and the calculation apparatus 9 corresponds to derivation unit. In addition, the stir bar 11 and the magnetic stirrer 12 correspond to stirring apparatuses.

It should be noted that the above-mentioned Examples according to the present invention have the following merits: 1) a general limulus reagent used in the turbidimetric method can be used without further treatments; 2) the configuration of the measurement system (measurement apparatus) can be simplified, and multi-channelization (8 to 16 ch) can be relatively easily performed; and 1) measurement can be completed in almost the same time period as that in the case of the colorimetric method using a special reagent.

REFERENCE SIGNS LIST 1 measurement system
2 light source
3 optical system for incident light
4 sample cell
5 optical system for outgoing light
6 light receiving element
7 amplifier circuit
8 filter for removing noises
9 calculation apparatus
10 display
11 stir bar
12 magnetic stirrer

What is claimed is:

1. A method of measuring a physiologically active substance derived from an organism, which is used for detecting the physiologically active substance in a sample or measuring a concentration of the physiologically active substance, by reacting the physiologically active substance in the sample with LAL which is a limulus amoebocyte lysate, comprising:
emitting light into a mixture of the sample and the LAL and obtaining intensity of scattered light generated from the mixture by the incident light, after mixing of the sample and the LAL; and
detecting the physiologically active substance in the sample or measuring the concentration of the physiologically active substance based on an increase rate of the scattered light intensity.

2. The method of measuring a physiologically active substance derived from the organism according to claim 1, wherein the detecting the physiologically active substance in the sample or the measuring the concentration of the physiologically active substance is performed based on the increase rate before a predetermined acute change in the increase rate of the scattered light intensity.

3. The method of measuring the physiologically active substance derived from the organism according to claim 1, wherein power density of the light entering the mixture is 50 mW/mm$^2$ or more.

4. The method of measuring the physiologically active substance derived from the organism according to claim 1, wherein a wavelength of the light entering the mixture is 300-800 nm.

5. The method of measuring the physiologically active substance derived from the organism according to claim 1, further comprising sampling and comparing a plurality of scattered light intensities obtained in a predetermined period and determining a minimum value of the intensities or a mode value of a histogram as scattered light intensity in the period, in obtaining the increase rate of the scattered light intensity.

6. The method of measuring the physiologically active substance derived from the organism according to claim 1, further comprising stirring the mixture in obtaining the scattered light intensity.

7. The method of measuring the physiologically active substance derived from the organism according to claim 6, wherein a rate of stirring of the mixture is 300-3000 rpm.

8. The method of measuring the physiologically active substance derived from the organism according to claim 1, wherein the physiologically active substance derived from the organism comprises endotoxin or β-D-glucan.

9. The method of measuring the physiologically active substance derived from the organism according to claim 2, wherein power density of the light entering the mixture is 50 mW/mm$^2$ or more.

10. The method of measuring the physiologically active substance derived from the organism according to claim 2, wherein a wavelength of the light entering the mixture is 300-800 nm.

11. The method of measuring the physiologically active substance derived from the organism according to claim 2, further comprising sampling and comparing a plurality of scattered light intensities obtained in a predetermined period and determining a minimum value of the intensities or a mode value of a histogram as scattered light intensity in the period, in obtaining the increase rate of the scattered light intensity.

12. The method of measuring the physiologically active substance derived from the organism according to claim 2, further comprising stirring the mixture in obtaining the scattered light intensity.

13. The method of measuring the physiologically active substance derived from the organism according to claim 12, wherein a rate of stirring of the mixture is 300-3000 rpm.

14. The method of measuring the physiologically active substance derived from the organism according to claim 2, wherein the physiologically active substance derived from the organism comprises endotoxin or β-D-glucan.

* * * * *